United States Patent [19]
Jarrell et al.

[11] Patent Number: 5,306,910
[45] Date of Patent: Apr. 26, 1994

[54] TIME MODULATED ELECTRIFIED SPRAY APPARATUS AND PROCESS

[75] Inventors: Joseph A. Jarrell, Newton Highlands, Mass.; Michael J. Tomany, North Groseenordal, Conn.; Douglas P. Wittmer, Upton, Mass.

[73] Assignee: Millipore Corporation, Bedford, Mass.

[21] Appl. No.: 866,605

[22] Filed: Apr. 10, 1992

[51] Int. Cl.$^5$ .............................................. H01J 49/10
[52] U.S. Cl. ..................................... 250/286; 250/286
[58] Field of Search ..................... 250/286, 288, 288 A

[56] References Cited

U.S. PATENT DOCUMENTS

3,668,383  6/1972  Carroll ................................ 250/288
4,542,293  9/1985  Fenn et al. ........................... 250/288
4,999,493  3/1991  Allen et al. ....................... 250/288 A
5,070,240  12/1991  Lee et al. ............................ 250/286

Primary Examiner—Jack I. Berman
Attorney, Agent, or Firm—Andrew T. Karnakis; Paul J. Cook

[57] ABSTRACT

A system for forming a time modulated electrospray from a sample solution is provided. Further systems for analyzing this time modulated electrospray are provided. In a preferred such further system, a grid connected to a time modulated voltage source is provided between an electrospray apparatus and an analytical apparatus. More generally, a system for changing the energy of charged particles in a gas comprising the application of time modulated electric fields is provided.

18 Claims, 6 Drawing Sheets

TIME MODULATED ELECTRIFIED SPRAY APPARATUS AND PROCESS

BACKGROUND OF THE INVENTION

This invention relates to the generation for a time-modulated electrospray. Electrosprays are useful for analyzing solutes in a sample solution. More particularly the present invention provides a method and apparatus for intermittently forming an electrospray from a sample solution which is subsequently analyzed.

A liquid flowing through a capillary jet or orifice may be converted to a spray of small charged droplets (of the order of 1 μm in diameter) by applying a strong electric field to the liquid as it emerges from the tip of the capillary. For sufficiently high applied field, the electrostatic stress imposed by the field and the surface-induced electrical charge is sufficient to overcome the surface tension forces on the liquid. Breaking apart into a large number of small charged droplets is a way for the liquid to disperse the charge and reach a lower total energy state. This process of forming a spray is commonly known as electrospray.

Previous applications of the electrospray process to mass spectrometry regard electrospray as a steady-state process. The applied electric field referred to above is kept constant in time and, as a result, spray formation is constant in time. In a recent abstract on coupling electrospray to a time-of-flight mass spectrometer, Whitehouse, et al state that electrospray is an inherently DC phenomenon, requiring the continuous presence of a strong potential gradient about a sharp needle tip to form charged droplets, "Electrospray ionization on an ion storage time-of-flight mass spectrometer" J. G. Boyle et al, extended abstracts from the 12th International Mass Spectrometry Conference, Aug. 26-30, 1991 in Amsterdam, Holland, abstract #WeM-DO4 on p. 238.

At the present time apparatus are available for forming an electrospray of a sample solution such as a liquid stream effluent from a liquid chromatography separation step and subsequently analyzing the electrospray with a mass analyzer such as a quadrupole mass spectrometer, an ion trap, a time-of-flight mass spectrometer or a magnetic sector mass spectrometer or the like. In any kind of mass spectrometer (MS) manipulation of analysis that requires a finite time to accomplish or in which ions need to be stored whether prior to or as part of the analysis, such as in a time-of-flight mass spectrometer, a quadrupole ion trap, many implementations of MS/MS, or a Fourier Transform mass spectrometer, a non-continuous source of the electrospray can provide increased efficiency of analysis. Thus, for example in the case of an ion trap, ions are accumulated and stored in a small volume by appropriate electric fields. The mass-to-charge spectrum of these accumulated ions cannot be ascertained until the trap is "swept clean", i.e., voltages are applied to the trap that sequentially cause ions to be ejected and detected. It is only by virtue of the parameters that cause their ejection that their mass-to-charge ratio is known. During this readout interval, newly formed electrospray ions cannot efficiently be introduced into the trap, thus, they are wasted. Similarly, a time-of-flight mass spectrometer analyzes ions of different mass-to-charge ratio, by releasing or creating a burst of ions of a given energy, and then measuring the differences in their mass-to-charge ratio on the basis of their differing transit times along some predetermined trajectory. Newly created ions cannot be introduced during this transit period without potentially confusing the analysis. Thus, new ions generated during this transit time are wasted.

In most prior electrospray sources, the electrospray capillary must be maintained at a high electrical potential with respect to ground if the mass-to-charge analyzer and its vacuum housing is to be kept close to ground potential. This means that any means to introduce liquid to the electrospray source such as a liquid chromatograph or pump, must either also be maintained at a high electrical potential with respect to ground, or must be connected to the electrospray capillary by long lengths of narrow bore insulating tubing. This can compromise system performance as well as present something of a safety hazard.

In a liquid chromatograph, a stream of solvent, containing a mixture of chemical species in solution, is passed at elevated pressure through a chromatographic column. The column is so designed that it separates the mixture, by differential retention on the column, into its component species. The different species then emerge from the column as distinct bands in the solvent stream, separated in time. The liquid chromatograph provided therefore, an ideal device for the introduction into a mass spectrometer of single species, separated from initially complex mixtures.

It has been proposed in U.S. Pat. No. 4,542,293 to use a strong gas flow to entrain ions and droplets through a capillary composed of an insulator such that they migrate against the opposing electric field across that capillary, i.e., the viscous drag of the gas flow on these ions or droplets present is larger than the electrostatic force on the ions. A specific benefit of this arrangement is that it can allow the capillary, from which the electrospray emanates, and the mass analyzer to be maintained at relatively arbitrary electrical potentials, or most conveniently, they may be both at ground. In this system, however, charged droplets and ions may deposit on the inner wall of this insulated capillary. This charge then may leak away at an indeterminate rate which may affect interface stability.

Accordingly, it would be desirable to provide a method and apparatus for modulating the conversion of a liquid sample into a form such as an electrospray which permits subsequently analysis in a mass spectrometer or the like. In addition, it would be desirable to provide such an apparatus wherein the liquid sample can be converted to an electrospray and both apparatus for producing the electrospray and the electrospray analysis apparatus can be maintained at close to ground electrical potential. Such a method and apparatus would minimize sample waste and would provide a safe and efficient means for analyzing the sample.

SUMMARY OF THE INVENTION

The present invention provides a method and apparatus for forming a time modulated electrospray from a solution containing a solute sample. This method and apparatus utilize a time modulated electric field. A solution containing the sample is passed through a capillary and emerges from an exit end of the capillary where it is converted to a time modulated electrospray by the application of this time modulated electric field. The electrospray can then pass to an analyzer. The analyzer is capable of analyzing the mass to charge spectrum of the sample solute. By utilizing a time modulated electrospray the flow of sample can be modulated to accommodate the capacity of the analyzer to analyze ionized sample on an intermittent basis. Thus, the sample can be more efficiently analyzed. A further method and apparatus for analyzing a time modulated electrospray contains an element positioned between the electrospray means and the analyzer. A time modulated voltage can be applied to this element. This element contains at least one aperture through which the electrospray can pass. In a preferred embodiment, the electrical potential of the electrospray means can be maintained at ground, or close to ground, electrical potential since the electrical field driving force to effect electrospray flow between the capillary and the analyzer is provided by the intermediate time modulated voltage applied to this intermediate element.

BRIEF DESCRIPTION OF THE DRAWINGS

For the sake of clarity, only connections of time modulated voltages are shown in these figures, with the exception of FIG. 5.

DESCRIPTION OF SPECIFIC EMBODIMENTS

Figure 5:
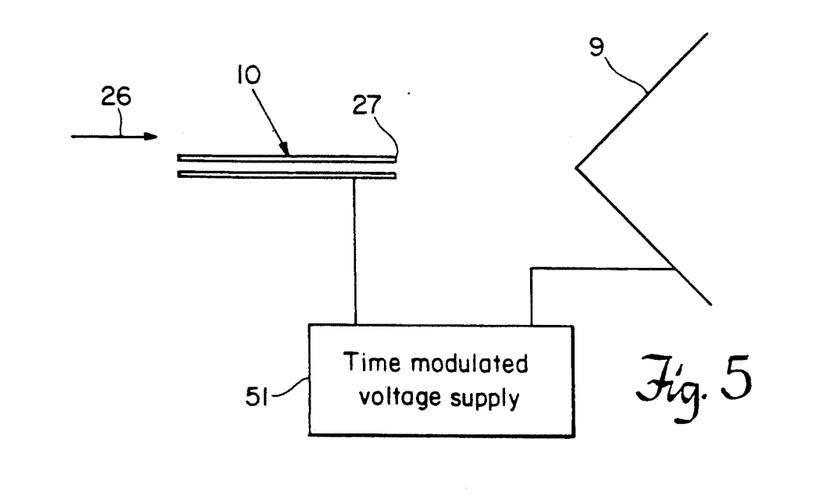
FIG. 5 illustrates a basic form of the invention.

The most general form of the present invention may be understood by reference to FIG. 5 which depicts a passageway 10 comprising typically an electrospray capillary and a reference element 9. In conventional electrospray, a constant electrical field is imposed on the tip region of the passageway 10 by applying a constant electrical potential difference between passageway 10 and element 9. In this invention, the constant electrical potential difference is replaced by a time modulated electrical potential difference, such as may be applied by a time modulated voltage supply 51, such that a time modulated electrospray is generated by a suitable choice of potentials. In a particular form, when element 9 provides a means of entry into an analytic device such as an ion trap or a time-of-flight mass spectrometer, sample in solution is not converted to an electrospray until the analytic device is ready to accept it. This enables more efficient analysis of sample. In addition by using a bipolar modulating electrical potential, both positively and negatively charged sprays can be generated essentially simultaneously. This is useful because some samples in solution are more efficiently analyzed from positively charged electrosprays, whereas other samples in solution are more efficiently analyzed from negatively charged electrosprays. This is particularly useful when a sample introduction means such as a liquid chromatograph is interfaced to a mass analyzer since it reduces by roughly two-fold, the time required for an analysis by both positive and negative electrospray. In conventional electrospray means, two repetitive liquid chromatographic separations would be required. With a time modulated electrospray, analysis of both positive and negative electrospray can be effected in one run. Since a typical chromatographic separation of a complex mixture of biomolecules can easily take an hour, this represents significant time savings.

In a preferred form of this invention, the portion of the electrospray which houses the liquid sample is formed from an electrically insulating material such as glass, quartz, synthetic polymeric composition or the like. The use of an electrically insulating material provides substantial advantage over the use of an electrically conductive material to house the liquid in the electrospray device such as stainless steel. In one mode of operation, the electrospray can be effected at low voltages with a capillary or jet having a small outer diameter in the order of 10 $\mu$m to 20 $\mu$m. Electrospray can be produced at an applied potential difference as low as about 775 volts between the electrospray device exit and the nearest reference electrode. In a second mode of operation, it is desirable to maintain as high a voltage differential as possible between the exit end of an electrically insulated electrospray device and the housing. A high voltage of up to about 18 kilovolts (KV) can be used with the nonconducting electrospray. When operating in this manner, high throughputs of electrospray of up to about 20 $\mu$L/min can be achieved while avoiding arcing between the electrospray device and the housing. This flexibility in operation permits the apparatus of this invention to be utilized within a wide range of operating conditions, including the electrospraying of solutions of higher water content (as high as 97% v/v).

A further preferred embodiment provides the advantage that it enables both the electrospray device and an analytical device to both be maintained at electrical potentials that are at or near ground. With most conventional electrospray means either the electrospray device or the analyzing device must be maintained at a high voltage. More generally this embodiment permits a more arbitrary relationship between the electrical potentials imposed on the electrospray device and the analyzer.

Figure 6:
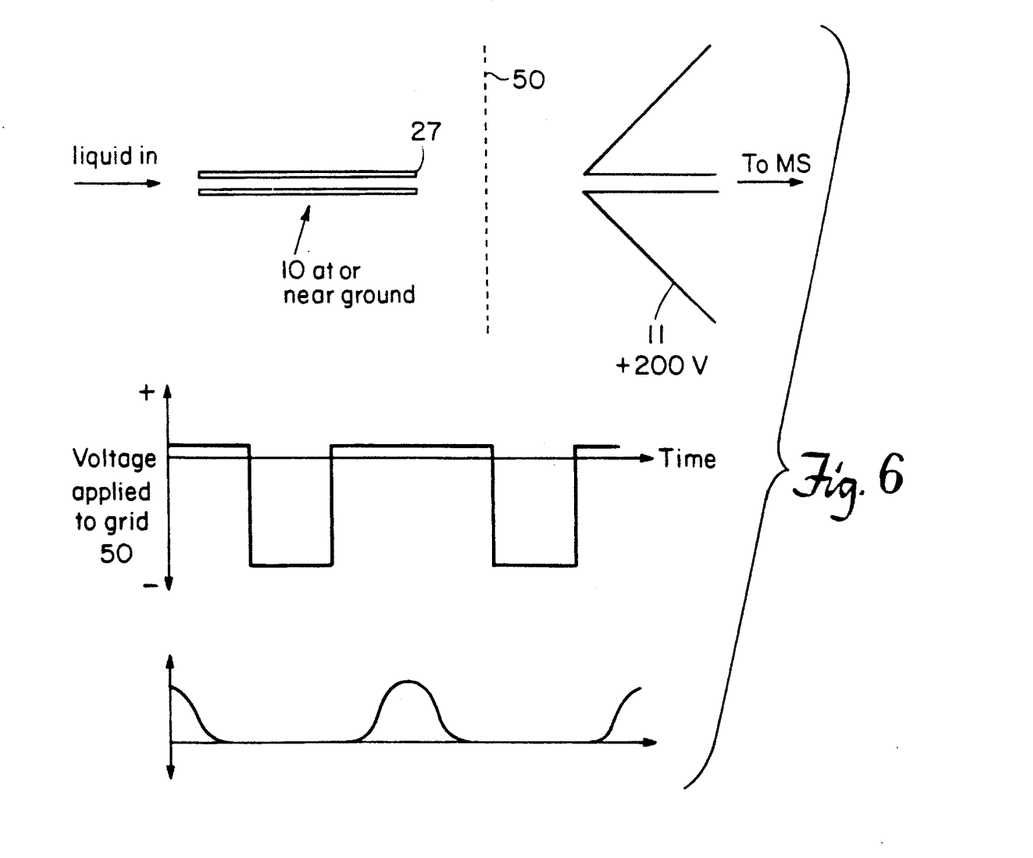
FIG. 6 illustrates the ion signal recorded as a function of a time modulated voltage applied to an element between a passageway and a housing interfaced to an analytical device.

This is accomplished by interposing another element between the electrospray device and the analyzer and may be understood by reference to FIG. 6.

The following describes the electrical potentials used to form positive electrosprayed ions, but the process is the same for negative ion formation except that the polarity of the applied potentials typically needs to be reversed.

Referring to FIG. 6, the passageway 10 may be kept at ground or near ground potential at all times. Likewise the entrance to an analytical device, which may typically be a housing 11, may also be kept at ground or more typically at a few hundred volts positive with respect to ground at all times. A grid 50 is interposed as shown in FIG. 6 between the passageway 10 and housing 11. The electrical potential applied to the grid 50 is modulated as shown schematically in FIG. 6. First a negative potential is applied (typically of a few Kilovolts) to grid 50. This imposes a field on the fluid emerging from the exit end 27 of passageway 10 that induces positive charge on that fluid resulting in an electrospray of positively charged droplets. These droplets then migrate towards grid 50 and some of these droplets, and some of any ions already formed, pass through grid 50 because of their momentum. If this negative potential on grid 50 were maintained, droplets and any ions present would ultimately come to rest on the grid 50.

After a short duration of time, however, (typically between 50 and 5000 microseconds), the polarity of the electrical potential imposed on grid 50 is reversed to a value which is typically a few hundred volts positive with respect to the housing 11, such that ions and droplets that have passed through grid 50 are now driven towards housing 11 by the field between housing 11 and grid 50. Some ions or droplets which are close to grid 50, may not quite have yet traversed grid 50 at the moment the applied potential swings positive. The momentum they possess, however, may nevertheless be sufficient to carry them through grid 50.

Figure 7:
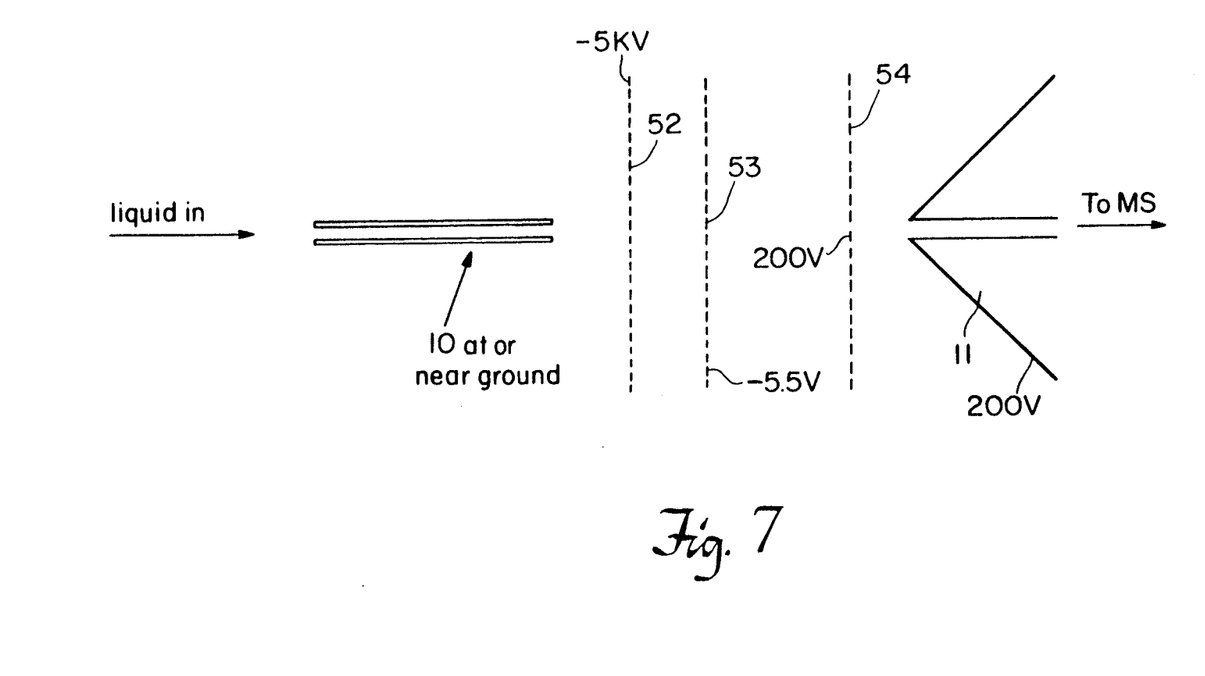
FIG. 7 illustrates the use of multiple grids in the apparatus of this invention.

It will be evident to those skilled in the art that it is possible to add additional grids and modulating voltages to the same effect, in essence forming a peristaltic pump, effect for charged particles. It will also be evident that these techniques can also be used with grids that are not perfectly parallel i.e. to cause charged particles to turn corners. Specifically the element interposed between the passageway 10 and the housing 11 need not be limited to a grid, but could also be any partially transmissive electrode, e.g. an annulus. An example of a variation of applying time-modulated voltages to grids or electrodes which permits setting both the electrospray capillary and the mass-to-charge analyzer at or near ground potentials, is depicted in FIG. 7. Here, the electrospray is on continuously but the modulation of the potential applied to the interposed grids allows electrosprayed droplets and ions to migrate from the passageway 10 to the housing 11.

It will also be evident to those skilled in the art that time modulated electric fields may be usefully employed to likewise change the energy state of electrically charged particles that may be generated by other techniques well known to those versed in the art. Examples of such techniques are nebulization techniques that employ thermal, pneumatic, ultrasonic, means, or various combinations thereof. Some of these examples are frequently referred to by their trade names as Ionspray and Thermospray. More generally, it will be recognized that while the above descriptions of these techniques are based on the charged particles in question being in a gaseous medium, these techniques also may usefully be employed in other fluid mediums. It should also be recognized that while this invention might most typically be used as described above, to permit both the electrospray capillary and the mass-to-charge analyzer and its vacuum housing to be kept close to ground, the same principles could be use to raise the electrical potential at which droplet or ions find themselves so as to facilitate their optimal introduction into a magnetic sector mass spectrometer. Similarly, it will be recognized that other voltage time profiles are applicable. In the examples described here, the modulating voltages make discrete, level shifts in time, i.e. they are depicted by rectangularly shaped pulses. This invention can also be implemented, for example, with sinusoidal voltage time variations or many other periodic or roughly periodic variations of voltage in time.

Several specific embodiments detailing complete electrospray, interface, and mass analysis systems are described below with reference to FIGS. 1, 2, 3, and 4. These systems provide for the generation of electrosprays from sample solutions, and desolvation of these electrosprays to form intact ion streams consisting of ions, vapor and gas for analysis In the following, all processes described are based on the electrical potential which would be applied for the formation of positively charged droplets, ions and clusters. It will be evident that by suitable reversals of potentials, negatively charged droplets, ions and clusters can also be formed.

Referring to FIG. 1, the liquid to be electrosprayed (typically carrying analyte molecules of interest such as from a liquid chromatograph) flows, in the direction shown by the arrow 26, into one end of the passageway 10 which may be kept at or near electrical ground potential at all times. As it emerges from the other end of this capillary, the liquid is converted to a time modulated electrospray, as described above, by virtue of the time modulated electrical potential difference between the exit end 27 at the tip of passageway 10 and grid 50 which is connected to time modulated voltage supply 51. This end 27, from which the liquid is electrosprayed, and grid 50 are positioned roughly opposite a heated electrically conductive housing 11. Housing 11 forms a wall of chamber 32, which consists of housing 11, wall portion 8, skimmer 15 and two insulating portions 7. Housing 11 is electrically insulated by an insulating portion 7 from its surrounds and thus may be set at an arbitrary electrical potential with respect to ground. Housing 11 is traversed by a passageway 1 and includes a heater 31 such as an electrical cartridge heater. Passageway 1 has an entrance orifice 12 and an exit orifice 28. The entrance orifice 12 of passageway 1 is positioned at the apex of housing 11. Typically, the length of the passageway is between about 1 and 4 cm. The housing 11 is formed of an electrically and thermally conductive material such as aluminum which is heated to a temperature between about 65° C. and 220° C., preferably between about 100° C. and 130° C. The housing 11 can be formed of a metal such as aluminum or stainless steel. The housing 11 can be heated by any conventional means such as by electrical resistance heaters 31 imbedded in the housing or by internal conduits for heated heat exchange fluid. In any event, uniform heating of the passageway can be easily effected due to its mass and material of construction. The passageway 1 through housing 11 may be contoured in such a way as to reduce the need for precise positioning of the exit end 27 with respect to the housing 11 and to optimize thermal transfer from the housing 11 to the ion stream. The housing 11 also serves as a wall between a region of atmospheric pressure 13 and a region of lower pressure 14.

Region 14, is maintained at this lower pressure, typically 4–20 Torr by the action of a small rotary pump 6. The housing 11 is typically maintained at a temperature of from 100–220 C. The pressure drop across it causes the ambient atmosphere in region 13 to be drawn into the orifice 12. This gas flow, in conjunction with the electric fields between the grid 50 and the housing 11, causes some of the electrosprayed droplets, ions, clusters and vapors to enter orifice 12 and enter passageway 1. As these droplets pass through the passageway 1, heat is transferred to them thus promoting desolvation and some ion evaporation. The housing 11 has sufficient mass, typically greater than about 50 g, to effect this heat transfer. The housing 11 used in conjunction with the grid 50 having a time modulated voltage applied to it, constitutes a preferred embodiment of this invention.

Region 14 is bounded by housing 11, skimmer 15 and wall portion 8. In a preferred embodiment, they are all electrically isolated from each other, by insulating portions 7, such that the shape of wall portion 8, and the electrical potential applied to it, can be used to optimize charged particle transmission. It is, however, also possible for wall portion 8 to be electrically part and/or mechanically part of either housing 11 or skimmer 15. The distance between the exit orifice 28 of passageway 1 and the orifice 16 of skimmer 15 is typically between about 0.1 and 0.5 cm.

The ion stream of air, droplets, ions, gas, clusters, and vapor emerges from orifice 28 into region 14 and impinges on a conductive skimmer 15 that is electrically insulated from its surrounds and thus may be set at an arbitrary electrical potential with respect to ground.

Typically it operates at a potential such that there exists an electrical field between housing 11 and skimmer 15 that tends to focus charged particles towards skimmer 15. Because collisions between charged ion stream components (e.g. ions, charged droplets, charged clusters and solvated ions) and neutral gas and vapor molecules occur in this region 14 as the ion stream traverses region 14 on their way to skimmer 15, additional desolvation, ion evaporation and declustering occur. The energy of these collisions can be affected by the potential difference between the housing 11 and skimmer 15.

A portion of the ion stream arriving at skimmer 15 traverses the orifice 16 at its apex and enters region 17 and impinge on a conductive skimmer 18 that is electrically insulated from its surrounds and thus may be set at an arbitrary electrical potential with respect to ground. Region 17 is maintained at a lower pressure, typically 0.1-3 Torr by another rotary pump 4. Again, because collisions between charged ion stream components (e.g. charged droplets, charged clusters and solvated ions) and neutral gas and vapor molecules occur in this region 17 as the ion stream traverses it on its way to skimmer 18, additional desolvation and ion evaporation occurs.

Because of the lower pressure in this region, the energy of these collisions is considerably affected by the potential difference between skimmer 15 and skimmer 18 such that considerable desolvation and ion evaporation may occur. The energy of collisions in this region can be controlled by the electrical potential difference between these regions. Indeed these collisions can be sufficiently energetic that fragmentation of ionized analyte molecules can occur providing useful structural information.

Region 17 is bounded by skimmer 15, skimmer 18 and wall portion 5. In a preferred embodiment, they are all electrically isolated from each other by insulating portions 7, such that the shape of wall portion 5, and the electrical potential applied to it, can be used to optimize charged particle transmission. It is however, also possible for wall portions 5 to be electrically part and/or mechanically part of either skimmer 15 or skimmer 18.

A portion of the ion stream arriving at skimmer 18 traverses an orifice 19 at the apex of skimmer 18 and enters region 20. Region 20 is typically separated from the region 21 containing a mass analyzer 22 and each region is separately pumped but this is not mandatory. In other embodiments, regions 20 and 21 may not be separated. In either case, ion optics 24 are contained in region 20 that serve to focus ions, emerging into region 20, via orifice 19, onto the entrance aperture 25 of the mass analyzer 22. Typically, this can be a quadrupole mass spectrometer, an ion trap, a time-of-flight mass spectrometer or a magnetic sector mass spectrometer.

Figure 1:
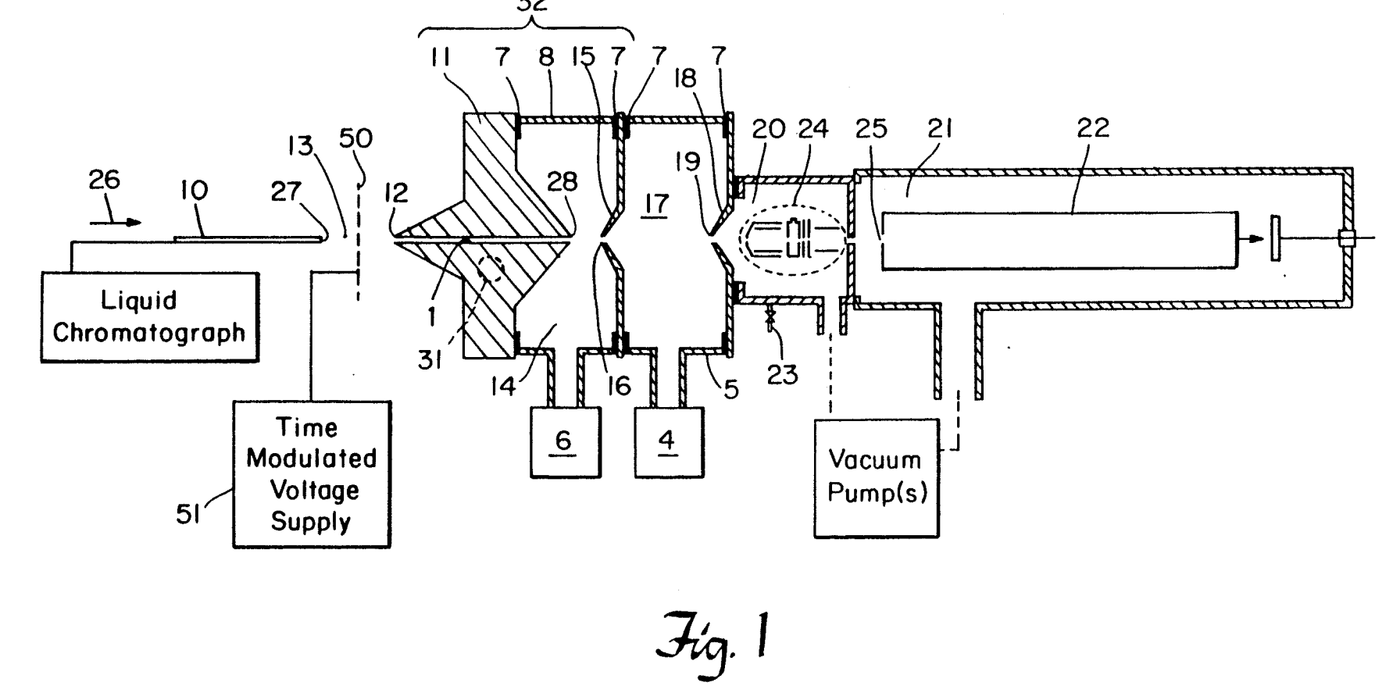
FIG. 1 is a schematic view of a preferred apparatus of this invention.

In a preferred embodiment, however, shown in FIG. 1, these ion optics are also designed such that they can also serve to ionize neutral gas molecules, introduced into region 20 through leak valve 23, by conventional electron impact ionization. The benefit provided by this arrangement is that the mass axis of the mass analyzer may be calibrated with well-known, easily purified, low molecular weight compounds, typically perfluorotributylamine.

Figures 2, 2A:
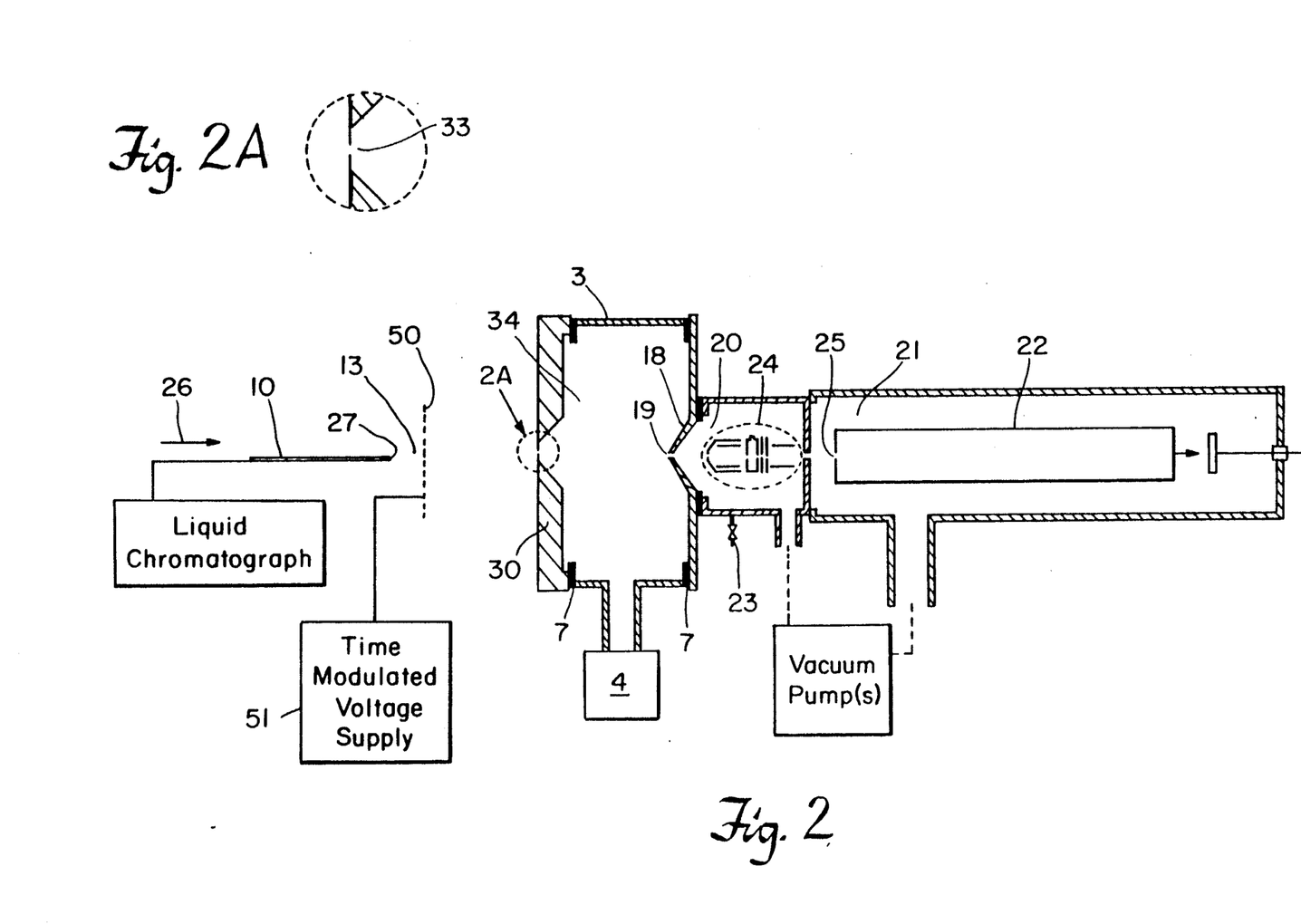
FIGS. 2 and 2A are schematic views of an alternative apparatus of this invention.
Figure 3:
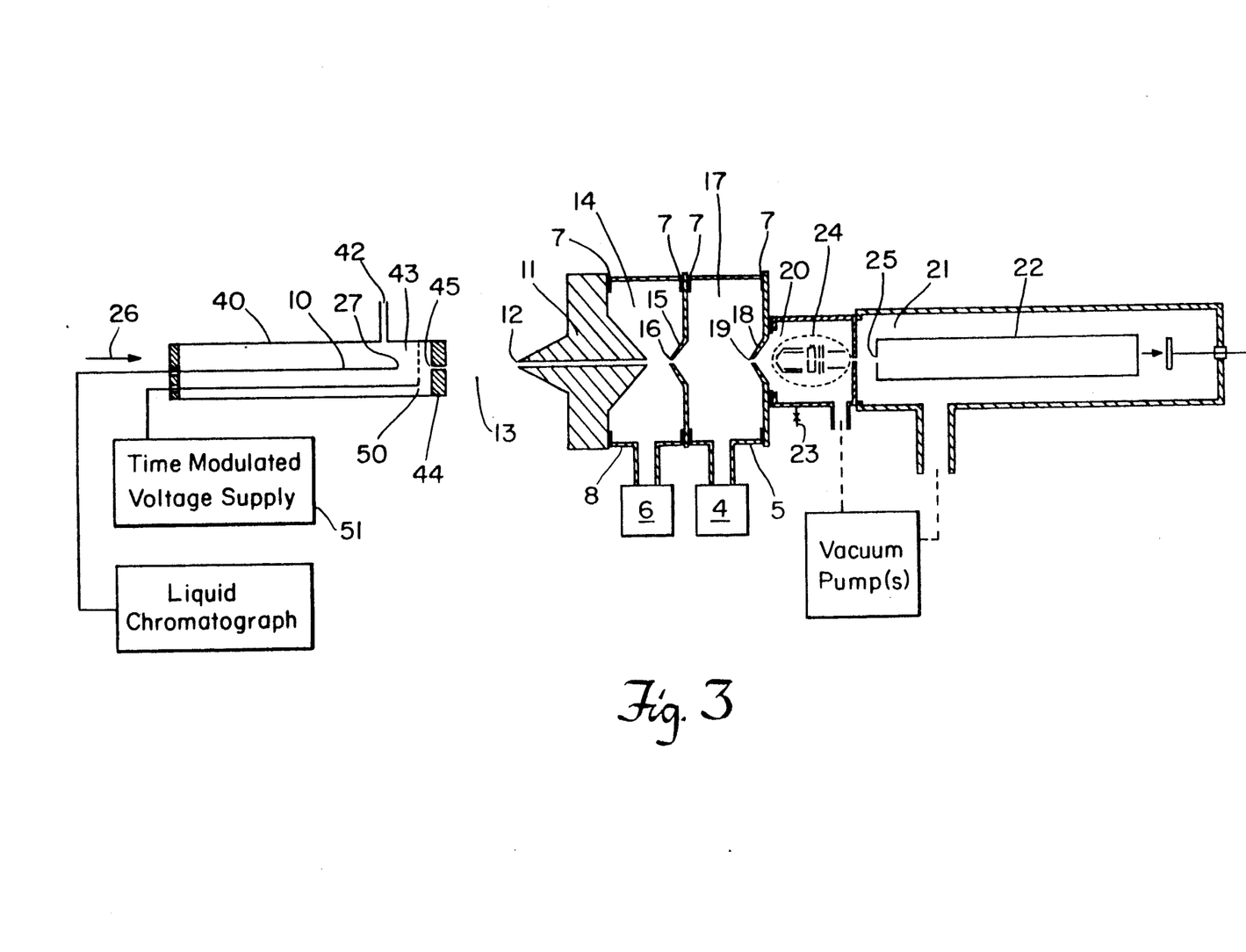
FIG. 3 is a schematic view of an alternative apparatus of this invention wherein the electrospray capillary is positioned within a chamber.
Figure 4:
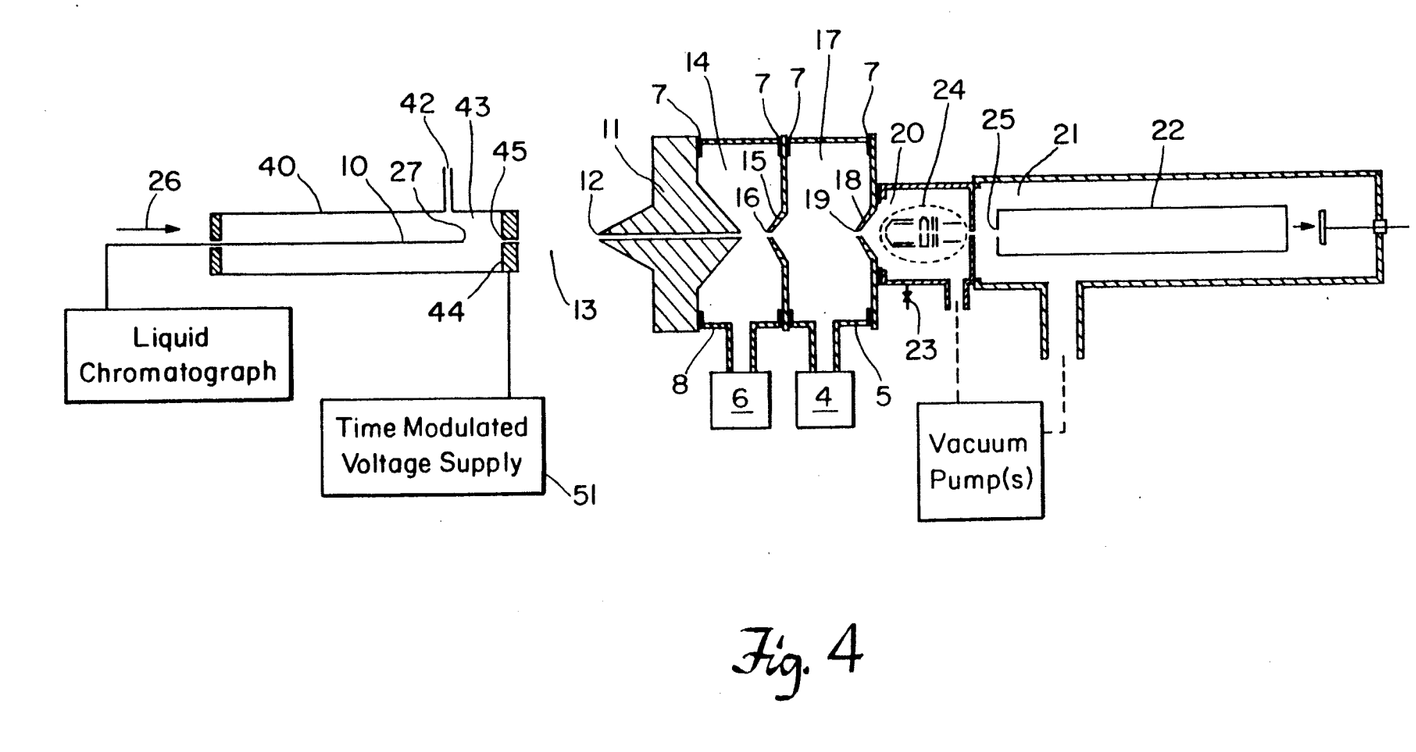
FIG. 4 is a schematic view of an alternative apparatus of this invention wherein a portion of the chamber is connected to a time modulated voltage supply.

For the sake of simplicity, those elements of FIGS. 2, 3 and 4 that are in common with their counterparts in FIG. 1 retain the same reference numerals.

Referring to FIG. 2, the liquid to be electrosprayed (typically carrying analyte molecules of interest such as from a liquid chromatograph) flows, in the direction shown by the arrow 26, into one end of the passageway 10 which may be kept at or near electrical ground potential at all times. As it emerges from the other end of this capillary, the liquid is converted to a time modulated electrospray, as described above, by virtue of the time modulated electrical potential difference between the exit end 27 at the tip of passageway 10 and grid 50 which is connected to time modulated voltage supply 51. This end 27, from which the liquid is electrosprayed, and the grid 50 are positioned roughly opposite a conductive plate 30 that is electrically isolated by insulating portions 7 from its surrounds and thus may be set at an arbitrary electrical potential with respect to ground. Plate 30 contains an orifice 33. Plate 30 also serves as a wall between a region of atmospheric pressure 13 and a region of lower pressure 34. Region 34 is maintained at this lower pressure, typically 0.5-3 Torr by the action of a small rotary pump 4. No heat need to applied to plate 30. Plate 30 can be maintained at room temperature. The pressure drop across plate 30 causes the ambient atmosphere in region 13 to be drawn through orifice 33. This gas flow, in conjunction with the electric field between the passageway 10 and plate 30, causes some of the electrosprayed droplets and ions to enter orifice 33.

This stream of air, droplets, ions and vapor emerges from orifice 33 into region 34 and impinges on a conductive skimmer 18 that is electrically insulated from its surrounds by insulated portions 7 and thus may be set at an arbitrary electrical potential with respect to ground. Typically, it operates at a potential such that there exists an electric field between plate 30 and skimmer 18 that tends to focus charged particles towards skimmer 18. Because of collisions of both charged ion stream components with neutral gas and vapor molecules occur in this region 34 as these droplets and solvated ions traverse it on their way to skimmer 18, considerable desolvation and ion evaporation occurs such that a usable ion signal can be produced.

Because of the low pressure in this region, the energy of these collisions is considerably affected by the potential difference between plate 30 and skimmer 18, such that considerable desolvation and ion evaporation occur. The energy of collisions in this region can be controlled by the electrical potential difference between these regions. Indeed, these collisions can be sufficiently energetic that fragmentation of ionized analyte molecules can occur providing useful structural information.

Region 34 is bounded by plate 30, skimmer 18 and wall portion 3. In a preferred embodiment, they are all electrically isolated from each other by insulating portions 7, such that the shape of wall portion 3, and the electrical potential applied to it, can be used to optimize charged particle transmission. It is, however, also possible for wall portion 3 to be electrically part and/or mechanically part of either plate 30 or skimmer 18.

Some portion of the ions and droplets arriving at skimmer 18 traverse the orifice 19 at its apex and enter region 20. Region 20 is ideally separated from the region 21 containing the mass spectrometer 22, and each region is usually separately pumped, but this is not mandatory. In other embodiments, regions 20 and 21 are not separated. In either case, ion optics 24 are contained in region 20 that serve to focus ions, emerging into region 20 (via orifice 19), onto the entrance aperture 25 of the mass analyzer 22. Typically this is a quadrupole mass spectrometer, an ion trap, a time-of-flight spectrometer or a magnetic sector mass spectrometer. In a preferred embodiment, however, shown in FIG. 2 these ion optics are also designed such that they can also serve to ionize neutral gas molecules, introduced into region 20 through leak valve 23, by conventional electron impact ionization. The benefit provided by this arrangement is that the mass axis of the mass analyzer may be calibrated with well-known, easily purified, low molecular weight compounds, typically perfluorotributylamine. Other specific benefits conferred by this design compared to previous designs are the elimination of the need for any external supply of gas, ease of disassembly and cleaning, and the ability to provide useful data with relatively modest rotary pumps. An additional feature of this scheme is that it is possible to use only one rotary pump to both evacuate region 34 and provide backing pumping for the turbomolecular or diffusion pumps needed to evacuate regions 20 and 21.

Referring to FIG. 3, the liquid to be electrosprayed, typically carrying analyte molecules of interest, flows in the direction shown by the arrow 26 into one end of the passageway 10. As it emerges from the other end of this capillary, the liquid is converted to an electrospray by virtue of the electrical potential difference between the exit 27 at the tip of passageway 10 and grid 50 which is connected to time modulated voltage supply 51. This passageway 10 is positioned inside a chamber 40 which is maintained at a pressure roughly 6-12 psi above the outside ambient pressure in region 13 by a flow of gas introduced through entry port 42. This exit 27, from which the liquid is electrosprayed, and grid 50 are positioned roughly opposite a heated, electrically isolated conductive plug 44 containing orifice 45. It also serves as a wall between a region of atmospheric pressure 13 and a region of higher pressure 43. Plug 44 is ideally maintained at a temperature of 65-125 C. The pressure drop across it causes gas in region 43 to flow out through orifice 45. This gas flow, in conjunction with the electric field between the passageway 10 and plug 44, causes some of the electrosprayed droplets and ions to enter orifice 45. As these droplets pass through orifice 45, heat is transferred to them such that significant desolvation and ion evaporation can occur.

This ion stream of air, droplets, ions, clusters and vapor emerges from orifice 45 into region 13 and impinges on an electrically conductive housing 11 that is electrically insulated from its surrounds by insulating portions 7 and thus may be set at an arbitrary electrical potential with respect to ground.

Region 14 is bounded by housing 11, skimmer 15 and wall portion 8. In a preferred embodiment, they are all electrically isolated from each other by insulating portions 7, such that the shape of wall portion 8, and the electrical potential applied to it, can be used to optimize charged particle transmission. It is, however, also possible for wall portion 8 to be electrically part and/or mechanically part of either housing 11 or skimmer 15.

A portion of the ion stream arriving at skimmer 15 traverses the orifice 16 at its apex and enters region 17 and impinges on a conductive skimmer 18 that is electrically insulated from its surrounds and thus may be set at an arbitrary electrical potential with respect to ground. Region 17 is maintained at a lower pressure, typically 0.1-3 Torr by another rotary pump 4. Again, because collisions between charged droplets ion stream components and neutral gas molecules occur in this region 17 as the ion stream traverses in on its way to skimmer 18, additional desolvation and ion evaporation occurs.

Because of the lower pressure in this region, the energy of these collisions is considerably affected by the potential difference between skimmer 15 and skimmer 18 such that considerable desolvation and ion evaporation can occur. The energy of collisions in this region can be controlled by the electrical potential difference between these regions. Indeed these collisions can be sufficiently energetic that fragmentation of ionized analyte molecules can occur providing useful structural information.

Region 17 is bounded by skimmer 15, skimmer 18 and wall portion 5. In a preferred embodiment, they are all electrically isolated from each other by insulating portions 7, such that the shape of wall portion 5, and the electrical potential applied to it, can be used to optimize charged particle transmission. It is however, also possible for wall portions 5 to be electrically part and/or mechanically part of either skimmer 15 or skimmer 18.

Some portion of the ion stream arriving at skimmer 18 traverses an orifice 19 at the apex of skimmer 18 and enters region 20. Region 20 is typically separated from the region 21 containing the mass spectrometer 22 and each region is separately pumped but this is not mandatory. In other embodiments, regions 20 and 21 may not be separated. In either case, ion optics 24 are contained in region 20 that serve to focus ions, emerging into region 20, via orifice 19, onto the entrance aperture 25 of the mass analyzer 22. In a preferred embodiment, however, these ion optics are also designed such that they can also serve to ionize neutral gas molecules introduced into region 20 through leak valve 23 by conventional electron impact ionization. The benefit provided by this arrangement is that the mass axis of the mass analyzer may be calibrated with well-known, easily purified, low molecular weight compounds, typically perfluorotributylamine. The primary benefit conferred by this design is that those elements which require the most frequent cleaning are a separate assembly, not involving vacuum and hence can be cleaned without having to disturb the rest of the system.

Referring to FIG. 4, the apparatus is the same as that shown in FIG. 3 except that grid 50 is eliminated and the time modulated voltage supply 51 is connected to the plug 44 containing orifice 45. The remainder of the elements shown in FIG. 4 function in the manner described above with reference to FIG. 3.

A further useful embodiment of this invention is in combination with ion mobility detectors. Ion mobility detectors (IMD) are devices that detect separate gas phase ions on the basis on their gas phase mobilities. Typically ions are produced at the sample inlet end by one of a variety of processes: electron impact from electrons emitted from a Ni-63 source, electrospray, coronaspray or ion-molecule reactions.

A coronaspray is generated with equipment that is similar to that used for electrospray, except that the applied field is so high that a continuous electrical breakdown is produced. This process produces predominantly singly charged ions. See, for example, "Coronaspray Nebulization and Ionization of Liquid Samples for Ion Mobility Spectrometry." C. B. Shumate et al, Analytical Chemistry, vol. 61, 1989, pp. 601–606.

These ions produced at the sample inlet end are then caused to drift through the drift tube by the imposed electric field, typically against an opposing flow of dry, heated gas until they arrive at the gate. The gate is pulsed electrically in such a way as to release a pulse of ions into the second section of the drift tube where the ions in the pulse can be separated on the basis of their mobilities. On arriving at the collector end of the drift tube the ions are detected by measuring the electrical current that they cause to flow when they impinge on a collector.

The generation of bursts of time-modulated electrospray or coronaspray ions by applying a time-modulated electric field to the tip of an electrospray or coronaspray capillary can confer two major benefits. It eliminates the need for a gate in an IMD which is a mechanically complex and expensive part to construct. It can also increase the efficiency of detection by reducing the effect of the duty cycle of the gate and the loss of ions at the gate. Thus the specific use of time-modulated electrospray or coronaspray in conjunction with an ion mobility detector is an object of this invention.

We claim:

1. Apparatus for converting a solution containing a solute sample into ionized molecules for analysis of the sample which comprises
    a passageway for passing said solution therethrough, said passageway having an exit to discharge said solution from said passageway in the form of an electrospray,
    means of generating a time modulated electric field in the vicinity of said exit of said passageway thereby, to time modulate the formation of said electrospray.

2. The apparatus of claim 1 wherein said passageway comprises a capillary tube.

3. The apparatus of claim 2 wherein said capillary tube is formed of an electrically nonconducting material.

4. The apparatus of claim 2 which includes analytical apparatus for detecting the presence of charged particles downstream of said passageway.

5. The apparatus of claim 3 which includes analytical apparatus for detecting the presence of charged particles downstream of said passageway.

6. The apparatus of claim 1 which includes analytical apparatus for detecting the presence of charged particles downstream of said passageway.

7. The apparatus of claim 6 which includes an electrically and thermally conductive housing interposed between said element and said analytical apparatus, said housing including a heated second passageway through the thickness of said housing to effect conversion of said electrospray to a desolvated ion stream, said housing having dimension to form a part of a chamber maintained under vacuum and said chamber including a skimmer interposed between said housing and said analytical apparatus.

8. The apparatus of claim 7 wherein said housing and said skimmer are electrically insulated from each other.

9. The apparatus of claim 7 wherein said housing, skimmer and analytical apparatus are electrically insulated from each other.

10. The apparatus of claim 7 wherein said passageway in said housing has a constant diameter.

11. The apparatus of claim 7 wherein said passageway in said housing has a varying diameter.

12. Apparatus for transferring charged particles from a first region in a fluid medium into a second region in a fluid medium, transfer of said charged particles being opposed by an electrical potential difference between said first region and said second region, comprising:
    an element intermediate said first region and said second region,
    and means to apply a time modulated electrical potential to said element thereby to effect transfer of said charged particles from said first region to said second region.

13. The apparatus of claim 12 further comprising a plurality of said elements, each of said elements including means to apply a time modulated electrical potential.

14. The apparatus of claim 13 wherein said elements are essentially parallel to each other.

15. The apparatus of claim 13 wherein said elements are arranged nonparallel to each other thereby to define a curved path for said charged particles.

16. Apparatus for converting a solution containing a solute sample into ionized molecules for analysis of the sample which comprises:
    a passageway for passing said solution therethrough, said passageway having an exit to discharge, into a first region in a fluid medium, said solution from said passageway being in the form of an electrospray,
    an element intermediate said first region and second region in said fluid medium,
    and means to apply a time modulated electrical potential to said element so as to generate a time modulated electric field in the vicinity of said exit of said passageway thereby to time-modulate the formation of said electrospray and to effect the transfer, from said first region into said second region, of said electrospray.

17. The apparatus of claim 16 which includes analytical apparatus for detecting the presence of charged particles downstream of said element.

18. The apparatus of claim 17 which includes an electrically and thermally conductive housing interposed between said element and said analytical apparatus, said housing including a heated second passageway through the thickness of said housing to effect conversion of said electrospray to a desolvated ion stream, said housing having dimension to form a part of a chamber maintained under vacuum and said chamber including a skimmer interposed between said housing and said analytical apparatus.

* * * * *